United States Patent
Kidron et al.

(10) Patent No.: US 9,186,412 B2
(45) Date of Patent: Nov. 17, 2015

(54) METHODS AND COMPOSITIONS FOR ORAL ADMINISTRATION OF INSULIN

(75) Inventors: Miriam Kidron, Jerusalem (IL); Ehud Arbit, Englewood, NJ (US)

(73) Assignee: Entera Bio Ltd., Jerusalem (IL)

( * ) Notice: Subject to any disclaimer, the term of this patent is extended or adjusted under 35 U.S.C. 154(b) by 0 days.

(21) Appl. No.: 13/058,259

(22) PCT Filed: Aug. 11, 2009

(86) PCT No.: PCT/IL2009/000786
§ 371 (c)(1),
(2), (4) Date: Feb. 9, 2011

(87) PCT Pub. No.: WO2010/020978
PCT Pub. Date: Feb. 25, 2010

(65) Prior Publication Data
US 2011/0142800 A1    Jun. 16, 2011

Related U.S. Application Data

(60) Provisional application No. 61/089,812, filed on Aug. 18, 2008.

(51) Int. Cl.
*A61K 38/28* (2006.01)
*A61K 47/12* (2006.01)
*A61K 9/20* (2006.01)
*A61K 9/48* (2006.01)

(52) U.S. Cl.
CPC ............... *A61K 47/12* (2013.01); *A61K 9/2013* (2013.01); *A61K 9/4858* (2013.01)

(58) Field of Classification Search
CPC ....................................................... A61K 38/28
USPC ...................... 514/5.9, 6.7, 6.8, 6.9
See application file for complete search history.

(56) References Cited

U.S. PATENT DOCUMENTS

| | | | |
|---|---|---|---|
| 4,579,730 | A | 4/1986 | Kidron et al. |
| 4,948,588 | A | 8/1990 | Kamiya et al. |
| 5,206,219 | A | 4/1993 | Desai |
| 5,773,647 | A | 6/1998 | Leone-Bay et al. |
| 5,824,638 | A | 10/1998 | Burnside et al. |
| 6,692,766 | B1 | 2/2004 | Rubinstein et al. |
| 6,858,576 | B1 | 2/2005 | Young et al. |
| 8,153,587 | B2 | 4/2012 | Ault et al. |
| 2005/0232981 | A1 | 10/2005 | Ben-Sasson |
| 2006/0045868 | A1 | 3/2006 | Meezan et al. |
| 2006/0122097 | A1 | 6/2006 | New |
| 2006/0178296 | A1 | 8/2006 | Goldberg et al. |
| 2006/0234913 | A1 | 10/2006 | Arbit et al. |
| 2007/0087957 | A1* | 4/2007 | Kidron .............................. 514/3 |

FOREIGN PATENT DOCUMENTS

| | | |
|---|---|---|
| JP | 2001-240558 | 4/2001 |
| JP | 2005-281231 | 10/2005 |
| JP | 2006-111558 | 4/2006 |
| WO | WO 2007/121471 | 10/2007 |
| WO | WO 2010/020978 | 2/2010 |

OTHER PUBLICATIONS

Alani, et al.; "Mechanistic Understanding of Oral Drug Absorption Enhancement of Cromolyn Sodium by an Amino Acid Derivative"; Pharmaceutical Research (2008); 25(1): 48-54.
Arbit, et al.; Oral Heparin: Status Review; Thrombosis Journal (2006); 4(6): 1-7.
Arora, et al.; "Promiscuous fatty acyl CoA ligases produce acyl-CoA and acyl-SNAC precursors for polyketide biosynthesis"; J Am Chem Soc. (2005); 127(26): 9388-9389.
Bar-On, H., et al.; "Enteral Administration of Inslin in the Rat"; Br. J. Pharmac. (1981); 73: 21-24.
Baughman, et al.; "Oral Delivery of Anticoagulant Doses of Heparin A Randomized, Double-Blind, Controlled Study in Humans"; Circulation—Journal of the American Heart Association (1998); 98: 1610-1615.
Beglinger, et al.; "Pharmacokinetics and Pharmacodynamic Effects of Oral GLP-1 and PYY3-36: A Proof-of-concept Study in Healthy Subjects"; Clinical Pharmacology & Therapeutics (2008); 84: 468-474.
Bendayan, et al.; "Morpho-cytochemical and biochemical evidence for insulin absorption by the rat ileal epithelium"; Diabetologia (1990); 33: 197-204.
Bendayan, et al.; "Biochemical and morpho-cytochemical evidence for the intestinal absorption of insulin in control and diabetic rats. Comparison between the effectiveness of duodenal and colon mucosa"; Diabetologia (1994); 37: 119-126.
Berkowitz, et al.; "Oral heparin administration with a novel drug delivery agent (SNAC) in healthy volunteers and patients undergoing elective total hip arthroplasty"; J Thromb Haemost. (2003); 1: 1914-1919.
Brayden, et al.; "Heparin absorption across the intestine: effects of sodium N-[8-(2-hydroxybenzoy)amino]caprylate in rat in situ intestinal instillations and in Caco-2 monolayers"; Pharm Res. (1997); 14(12): 1772-1779.
Cernea, et al.; "Comparison of pharmacokinetic and pharmacodynamic properties of single-dose oral insulin spray and subcutaneous insulin injection in healthy subjects using the euglycemic clamp technique"; Clinical Therapeutics (2004); 26(12): 2084-2091.
Cernea, et al.; "Dose-Response Relationship of Oral Insulin Spray in Healthy Subjects"; Diabetes Care (2005); 28(6): 1353-1357.
Cernea, et al.; "Dose-Response Relationship of an Oral Insulin Spray in Six Patients with Type 1 Diabetes: A Single-Center, Randomized, Single-Blind, 5-Way Crossover Study"; Clinical Therapeutics (2005); 27(10): 1562-1570.

(Continued)

*Primary Examiner* — Gyan Chandra

(57) ABSTRACT

This invention provides compositions comprising a protein, an absorption enhancer, a protease inhibitor, methods for treating diabetes mellitus, comprising administering same, and methods for oral administration of a protein with an enzymatic activity, comprising orally administering same.

21 Claims, 1 Drawing Sheet

(56) References Cited

OTHER PUBLICATIONS

Cole, et al.; "Challenges and opportunities in the encapsulation of liquid and semi-solid formulations into capsules for oral administration"; Advanced Drug Delivery Reviews (2008); 60: 747-756.
Ding, et al.; "Oral absorption enhancement of cromolyn sodium through noncovalent complexation" Pharm Res. (2004); 21(12): 2196-2206.
Goldberg, et al.; "Challenges for the oral delivery of macromolecules"; Nat Rev Drug Discov. (2003); 2(4): 289-295.
Gonze, et al.; "Orally administered heparin for preventing deep venous thrombosis"; Am J Surg. (1998); 176(2): 176-178.
Gonze, et al.; "Orally Administered Unfractionated Heparin With Carrier Agent Is Therapeutic for Deep Venous Thrombosis"; Circulation—Journal of the American Heart Associate (2000); 101: 2658-2661.
Hays, et al.; "Prevention and Treatment of Type 2 Diabetes: Current Role of Lifestyle, Natural Product, and Pharmacological Interventions"; Pharmacol. Ther. (2008); 118(2): 181-191.
Hess, et al.; "Investigation of the enhancing mechanism of sodium N-[8-(2-hydroxybenzoy)amino]caprylate effect on the intestinal permeability of polar molecules utilizing a voltage clamp method"; Eur J Pharm Sci. (2005); 25: 307-312.
Kidron, et al.; "A novel per-oral insulin formulation: proof of concept study in non-diabetic subjects"; Diabetic Medicine (2004); 21: 354-357.
Ma, et al.; "In vitro and in vivo evaluation of a novel oral insulin formulation"; Acta Pharmacologica Sinica (2006); 27(10): 1382-1388.
Maher, et al.; "Safety and efficacy of sodium caprate in promoting oral drug absorption: from in vitro to the clinic"; Advanced Drug Delivery Reviews (2009); 61: 1427-1449.
Malkov, et al.; "Oral delivery of insulin with the eligen technology: mechanistic studies"; Curr Drug Deliv. (2005); 2(2): 191-197.
Malkov, et al.; "Pathway of oral absorption of heparin with sodium N-[8-(2-hydroxybenzoy)amino] caprylate"; Pharm Res. (2002); 19(8): 1180-1184.
Money, et al.; "Development of oral heparin therapy for prophylaxis and treatment of deep venous thrombosis"; Cardiovasc Surg. (2001); 9(3): 211-218.
Mousa, et al.; "Pharmacokinetics and Pharmacodynamics of Oral Heparin Solid Dosage Form in Healthy Human Subjects"; The Journal of Clinical Pharmacology (2007); 47: 1508-1520.
Nissan, et al.; "Intestinal absorption of low molecular weight heparin in animals and human subjects"; Haemostasis (2000); 30: 225-232.
Pineo; et al.; "Orally active heparin and low-molecular-weight heparin"; Curr Opin Pulm Med. (2001); 7(5): 344-348.
Pineo, et al.; "Oral delivery of heparin: SNAC and related formulations" Best Pract Res Clin Haematol. (2004); 17(1): 153-160.
Qi; et al.; "Effect of casein and protamine on the enzymatic degradation and the orally hypoglycemic action of insulin"; Acta Pharmaceutica Sinica (2004); 39(10): 844-848.
Qi, et al.; "Gastrointestinal absorption enhancement of insulin by administration of enteric microspheres and SNAC to rats"; J Microencapsul. (2004); 21(1): 37-45.
Qi, et al.; "Studies on gastrointestinal absorption enhancement effect and mechanism of sodium N[8-(2-hydroxybenzyl)amino] caprylate to insulin solution"; Acta Pharmaceutica Sinica (2003); 38(12): 953-956.
Raz, et al.; "Rectal Administration of Insulin"; Israel Journal of Medical Sciences (1984); 20: 173-175.
Riley, et al.; "Peri- and Postnatal Developmental Toxicity of Salcaprozate Sodium (SNAC) in Sprague-Dawley Rats"; International Journal of Toxicology (2009); 28: 266-277.
Riley, et al.; "Subchronic Oral Toxicity of Salcaprozate Sodium (SNAC) in Sprague-Dawley and Wistar Rats"; International Journal of Toxicology (2009); 28: 278-293.
Rivera, et al.; "Oral delivery of heparin in combination with sodium N-[8-(2-hydroxybenzoy)amino]caprylate: pharmacological considerations"; Pharm Res. (1997); 14(12): 1830-1834.

Ross, et al.; "Gastrointestinal absorption of heparin by lipidization or coadministration with penetration enhancers" Curr Drug Deliv. (2005); 2(3): 277-287.
Welt, et al.; "Oral Heparin Prevents Neointimal Hyperplasia After Arterial Injury. Inhibitory Potential Depends on Type of Vascular Injury"; Circulation—Journal of the American Heart Association (2001); 104: 3121-3124.
Ziv, et al.; "Absorption of Protein via the Intestinal Wall A Quantitative Model"; Biochemical Pharmacology (1987); 36(7): 1035-1039.
Ziv, et al.; "Bile Salts Promote the Absorption of Insulin from the Rat Colon"; Life Sciences (1981); 29: 803-809.
Ziv, et al.; "Oral administration of insulin in solid form to nondiabetic and diabetic dogs"; Journal of Pharmaceutical Sciences (1994); 83(6): 792-794.
Formal Office Action Dated Jun. 29, 2011 From the Russian Agency for Industrial Property, Patent and Trade Marks (ROSPATENT), Federal Institute of Industrial Property of the Russian Federation Re. Application No. 2011108334 and Its Translation Into English.
Examination Report Dated Apr. 26, 2011 From the Intellectual Property Office Re. Application No. 591497.
International Preliminary Report on Patentability Dated Feb. 22, 2011 From the International Bureau of WIPO Re. Application No. PCT/IL2009/000786.
International Search Report and the Written Opinion Dated Jan. 12, 2010 From the International Searching Authority Re. Application No. PCT/IL2009/000786.
Pineo et al. "Oral Delivery of Ileparin: SNAC and Related Formulations", Best Practice & Clinical Research Haematology, 17(1): 153-160, 2004.
Pineo et al. "Orally Active Heparin and Low-Molecular-Weight Heparin", Current Opinion in Pulmonary Medicine, 7: 344-348, 2001.
Qi et al. "Effect of Casein and Protamine on the Enzymatic Degradation and the Orally Hypoglycemic Action of Insulin", Acta Pharmaceutica Sinica, 39(10: 844-848, 2004. Abstract in English.
Qi et al. "Studies on Gastrointestinal Absorption Enhancement Effect and Mechanism of Sodium N-[8-(2-Hydroxybenzyl)Amino] Caprylate to Insulin Solution", Acta Pharmaceutica Sinica, 38(12): 953-956, 2003. Abstract in English.
Riley et al. "Peri- and Postnatal Developmental Toxicity of Salcaprozate Sodium (SNAC) in Sprague-Dawley Rats", International Journal of Toxicology, 28(4): 266-277, Jul./Aug. 2009.
Riley et al. "Subchronic Oral Toxicity of Salcaprozate Sodium (SNAC) in Sprague-Dawley and Wistar Rats", International Journal of Toxicology, 28(4): 278-293, Jul./Aug. 2009.
Rivera et al. "Oral Delivery of Heparin in Combination With Sodium N-[8-(2-Hydroxybenzoyl)Amino]Caprylate: Pharmacological Considerations", Pharmaceutical Research, 14(12): 1830-1834, 1997.
Ross et al. "Gastrointestinal Absorption of Heparin by Lipidization of Coadministration With Penetration Enhancers", Current Drug Delivery, 2: 277-287, 2005.
Welt et al. "Oral Ileparin Prevents Neointimal Ilyperplasia After Arterial Injury: Inhibitory Potential Depends on Type of Vascular Injury", Circulation, 104: 3121-3124, 2001.
Response Dated Oct. 30, 2011 to Formal Office Action of Jun. 29, 2011 From the Russian Agency for Industrial Property, Patent and Trade Marks (ROSPATENT), Federal Institute of Industrial Property of the Russian Federation Re. Application No. 2011108334.
Examination Report Dated May 22, 2012 From the Intellectual Property Office of New Zealand Re. Application No. 591497.
Translation of Office Action Dated Jun. 20, 2012 From The State Intellectual Property Office of the People's Republic of China Re. Application No. 200980132155.8.
Office Action Dated Feb. 14, 2013 From the Israel Patent Office Re. Application No. 210842 and Its Translation Into English.
Translation of Office Action Dated May 3, 2013 From The State Intellectual Property Office of the People's Republic of China Re. Application No. 200980132155.8.
Request for Examination Dated Aug. 15, 2013 From the Russian Agency for Industrial Property, Patents and Trademark, Rospatent, Federal Institute of Industrial Property of the Russian Federation Re. Application No. 2013130611 and Its Summary in English.

(56) References Cited

OTHER PUBLICATIONS

Office Action Dated Oct. 30, 2013 From the Japanese Patent Office Re. Application No. 2011-523481 and Its Translation Into English.
Patent Examination Report Dated Aug. 15, 2013 From the Australian Government, IP Australia Re. Application No. 2009283821.
Examination Report Dated Apr. 26, 2011 From the Intellectual Property Office of New Zealand Re. Application No. 591497.
Communication Pursuant to Rules 70(2) and 70a(2) EPC Dated Dec. 3, 2013 From the European Patent Office Re. Application No. 09807991.6.
Supplementary European Search Report and the European Search Opinion Dated Nov. 14, 2013 From the European Patent Office Re. Application No. 09807991.6.
Office Action Dated Feb. 25, 2014 From The State Intellectual Property Office of the People's Republic of China Re. Application No. 200980132155.8 and Its Translation Into English.
Decision of Rejection Dated Sep. 10, 2014 From the Japanese Patent Office Re. Application No. 2011-523481 and Its Translation Into English.
Office Action Dated May 28, 2014 From the Israel Patent Office Re. Application No. 210842 and Its Translation Into English.
Office Action Dated Sep. 26, 2014 From The State Intellectual Property Office of the People's Republic of China Re. Application No. 200980132155.8 and Its Translation Into English.
Office Action Dated Jul. 20, 2015 From the Israel Patent Office Re. Application No. 210842.
Requisition by the Examiner Dated Jun. 4, 2015 From the Canadian Intellectual Property Office Re. Application No. 2,734,442.
Translation Dated Aug. 13, 2015 of Office Action Dated Jul. 20, 2015 From the Israel Patent Office Re. Application No. 210842.

\* cited by examiner

METHODS AND COMPOSITIONS FOR ORAL ADMINISTRATION OF INSULIN

This application is a U.S.C. §371 National Phase Application of International Application No. PCT/IL2009/000786, filed Aug. 11, 2009, which claims priority from U.S. Provisional Patent Application No. 61/089,812, filed Aug. 18, 2008, the contents of both of which are incorporated herein by reference.

FIELD OF INVENTION

This invention provides oral compositions comprising a protein, an absorption enhancer, and a protease inhibitor and a method for administering same.

BACKGROUND OF THE INVENTION

Due to improved biotechnology, the accessibility of biologically active peptides to the pharmaceutical industry has increased considerably. However, a limiting factor in the development of peptide drugs is the relative ineffectiveness when given perorally. Almost all peptide drugs are parenterally administered, although parenterally administered peptide drugs are often connected with low patient compliance.

Insulin is a medicament used to treat patients suffering from diabetes, and is the only treatment for insulin-dependent diabetes mellitus. Diabetes Mellitus is characterized by a pathological condition of absolute or relative insulin deficiency, leading to hyperglycemia, and is one of the main threats to human health in the 21st century. The global figure of people with diabetes is set to rise to 220 million in 2010, and 300 million in 2025. Type I diabetes is caused primarily by the failure of the pancreas to produce insulin. Type II diabetes, involves a lack of responsiveness of the body to the action of insulin.

Approximately 20%-30% of all diabetics use daily insulin injections to maintain their glucose levels. An estimated 10% of all diabetics are totally dependent on insulin injections.

Currently, the only route of insulin administration is injection. Daily injection of insulin is causes considerable suffering for patients. Side effects such as lipodystrophy at the site of the injection, lipatrophy, lilpohypertrophy, and occasional hypoglycemia are known to occur. In addition, subcutaneous administration of insulin does not typically provide the fine continuous regulation of metabolism that occurs normally with insulin secreted from the pancreas directly into the liver via the portal vein.

The present invention addresses the need for an alternate solution for administration of insulin and peptides such as insulin.

SUMMARY OF THE INVENTION

This invention provides, in one embodiment, a composition comprising a protein having a molecular weight of up to 100,000 Daltons, a protease inhibitor, and an absorption enhancer, wherein the absorption enhancer enhances the absorption of a protein through an intestinal mucosal barrier.

In another embodiment, the present invention provides a composition comprising a protein having a molecular weight of up to 100,000 Daltons, a protease inhibitor, and SNAC or SNAD.

In another embodiment, the present invention provides a method for oral administration of a protein having a molecular weight up to 100,000 Daltons to a subject, whereby a substantial fraction of said protein retains its activity after absorption, through an intestinal mucosal barrier of a subject, comprising administering orally to a subject a pharmaceutical composition comprising a protein, a protease inhibitor, and an absorption enhancer, wherein an absorption enhancer enhances the absorption of a protein through an intestinal mucosal barrier.

In another embodiment, the present invention provides a method for treating diabetes mellitus in a subject, comprising administering orally to a subject a pharmaceutical composition comprising insulin, Exenatide, or a combination thereof a protease inhibitor, and a absorption enhancer, wherein an absorption enhancer enhances the absorption of a protein through an intestinal mucosal barrier, thereby treating diabetes mellitus.

DETAILED DESCRIPTION OF THE INVENTION

Figure 1:
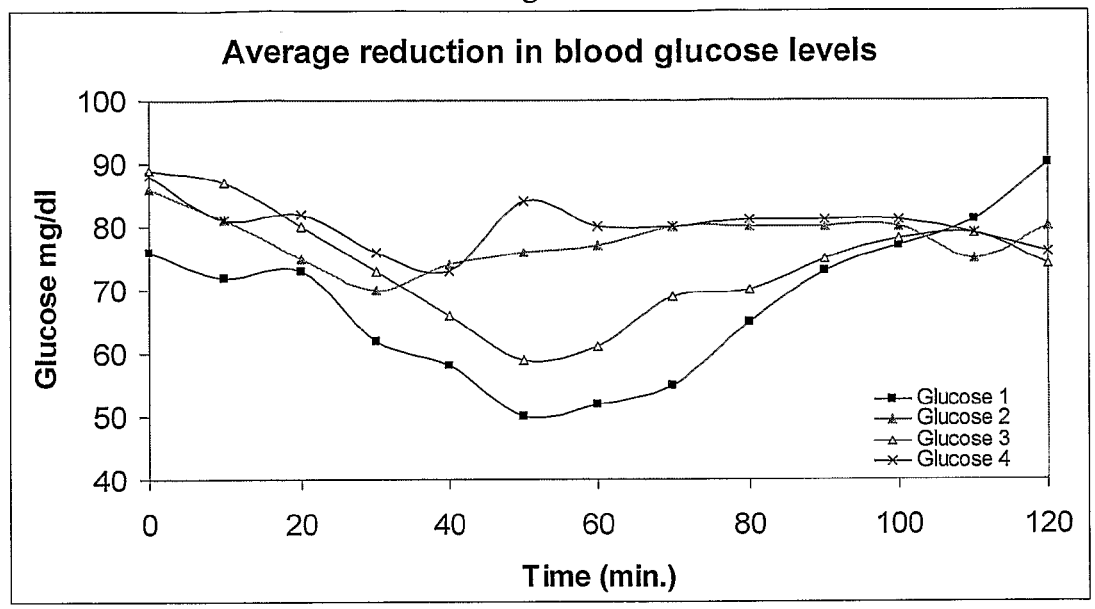
FIG. 1 is a graph showing the changes in blood glucose levels after treatment with the formulations of the invention.

This invention provides compositions and methods comprising a protein, a protease inhibitor, and a absorption enhancer. In another embodiment, the present invention provides compositions and methods comprising a protein having a molecular weight of up to 100,000 Daltons, a protease inhibitor, and a absorption enhancer. In another, embodiment, the absorption enhancer enhances the absorption of the protein through an intestinal mucosal barrier. In another, embodiment, the absorption enhancer enhances the absorption of a protein having a molecular weight of up to 100,000 Daltons through an intestinal mucosal barrier.

In another embodiment, the compositions of the present invention include an active agent, a protease inhibitor, and a carrier. In another embodiment, the compositions of the present invention are used to deliver various proteins through various biological, chemical, and physical barriers and are particularly suited for delivering proteins which are subject to environmental degradation. In another embodiment, the compositions of the present invention are used to deliver active proteins through various biological, chemical, and physical barriers and are particularly suited for delivering active proteins which are subject to environmental degradation. In another embodiment, the compositions comprise an active protein, SNAC, a protease inhibitor, and EDTA or Na-EDTA. In another embodiment, the compositions comprise an active protein, SNAC, a protease inhibitor, and an omega-3 fatty acid. In another embodiment, the compositions comprise an active protein, SNAC, a protease inhibitor, EDTA or Na-EDTA, and an omega-3 fatty acid. In another embodiment, the composition as described herein is an oral pharmaceutical composition. In another embodiment, the composition as described herein is an encapsulated oral pharmaceutical composition. In another embodiment, the composition as described herein is in a liquid oral dosage form. In another embodiment, the composition as described herein is in a dry oral dosage form (tablet etc.).

In another, embodiment, the protein of the present invention has a molecular weight of 1,000-5,000 Daltons. In another, embodiment, the protein of the present invention has a molecular weight of 5,000-10,000 Daltons. In another, embodiment, the protein of the present invention has a molecular weight of 10,000-20,000 Daltons. In another, embodiment, the protein of the present invention has a molecular weight of 20,000-30,000 Daltons. In another, embodiment, the protein of the present invention has a molecular weight of 40,000-50,000 Daltons. In another, embodiment, the protein of the present invention has a molecular weight of 50,000-60,000 Daltons. In another, embodiment, the protein of the present invention has a molecular weight of 60,000-70,000 Daltons. In another, embodiment, the protein of the present invention has a molecular weight of 70,000-80,000 Daltons. In another, embodiment, the protein of the present invention has a molecular weight of 80,000-90,000 Daltons. In another, embodiment, the protein of the present invention has a molecular weight of 90,000-100,000 Daltons. In another, embodiment, the protein of the present invention has a molecular weight of 100,000-150,000 Daltons.

In another embodiment, the protein has a molecular weight (MW) of 1-50 kilodalton (kDa). In another embodiment, the MW is 1-45 kDa. In another embodiment, the MW is 1-40 kDa. In another embodiment, the MW is 1-35 kDa. In another embodiment, the MW is 1-30 kDa. In another embodiment, the MW is 1-25 kDa. In another embodiment, the MW is 1-20 kDa. In another embodiment, the MW is 10-50 kDa. In another embodiment, the MW is 15-50 kDa. In another embodiment, the MW is 20-50 kDa. In another embodiment, the MW is 25-50 kDa. In another embodiment, the MW is 30-50 kDa. In another embodiment, the MW is 35-50 kDa. In another embodiment, the MW is 1-100 kDa. In another embodiment, the MW is 1-90 kDa. In another embodiment, the MW is 1-80 kDa. In another embodiment, the MW is 1-70 kDa. In another embodiment, the MW is 1-60 kDa. In another embodiment, the MW is 10-100 kDa. In another embodiment, the MW is 15-100 kDa. In another embodiment, the MW is 20-100 kDa. In another embodiment, the MW is 25-100 kDa. In another embodiment, the MW is 30-100 kDa. In another embodiment, the MW is 10-80 kDa. In another embodiment, the MW is 15-80 kDa. In another embodiment, the MW is 20-80 kDa. In another embodiment, the MW is 25-80 kDa. In another embodiment, the MW is 30-80 kDa. Each possibility represents a separate embodiment of the present invention.

In another embodiment, the MW is less than 20 kDa. In another embodiment, the MW is less than 25 kDa. In another embodiment, the MW is less than 30 kDa. In another embodiment, the MW is less than 35 kDa. In another embodiment, the MW is less than 40 kDa. In another embodiment, the MW is less than 45 kDa. In another embodiment, the MW is less than 50 kDa. In another embodiment, the MW is less than 55 kDa. In another embodiment, the MW is less than 60 kDa. In another embodiment, the MW is less than 65 kDa. In another embodiment, the MW is less than 70 kDa. In another embodiment, the MW is less than 75 kDa. In another embodiment, the MW is less than 80 kDa. In another embodiment, the MW is less than 85 kDa. In another embodiment, the MW is less than 90 kDa. In another embodiment, the MW is less than 95 kDa. In another embodiment, the MW is less than 100 kDa.

In another, embodiment, the protein of the present invention is insulin. In another embodiment, the insulin of methods and compositions of the present invention is human insulin. In another embodiment, the insulin is recombinant insulin. In another embodiment, the insulin is recombinant human insulin. In another embodiment, the insulin is bovine insulin. In another embodiment, the insulin is porcine insulin. In another embodiment, the insulin is whale insulin. In another embodiment, the insulin is a metal complex of insulin (e.g. a zinc complex of insulin, protamine zinc insulin, or globin zinc).

In another embodiment, the insulin is endogenous insulin. In another embodiment, the insulin is fast-acting insulin. In another embodiment, the insulin is lente insulin. In another embodiment, the insulin is semilente insulin. In another embodiment, the insulin is ultralente insulin. In another embodiment, the insulin is NPH insulin. In another embodiment, the insulin is glargine insulin. In another embodiment, the insulin is lispro insulin. In another embodiment, the insulin is aspart insulin. In another embodiment, the insulin is a combination of two or more of any of the above types of insulin. In another embodiment, the insulin is any other type of insulin known in the art. Each possibility represents a separate embodiment of the present invention.

In one embodiment, the amount of insulin utilized in the methods and compositions of the present invention is 0.5-3 units (u)/kg in humans. In one embodiment, the units used to measure insulin in methods and compositions of the present invention are USP Insulin Units. In one embodiment, the units used to measure insulin are milligrams. In another embodiment, one international Unit (IU) of Insulin is equivalent to 45.5 mg insulin.

In another embodiment, the amount of insulin is 0.1-1 u/kg. In another embodiment, the amount is 0.2-1 u/kg. In another embodiment, the amount is 0.3-1 u/kg. In another embodiment, the amount is 0.5-1 u/kg. In another embodiment, the amount is 0.1-2 u/kg. In another embodiment, the amount is 0.2-2 u/kg. In another embodiment, the amount is 0.3-2 u/kg. In another embodiment, the amount is 0.5-2 u/kg. In another embodiment, the amount is 0.7-2 u/kg. In another embodiment, the amount is 1-2 u/kg.

In another embodiment, the amount is 1.2-2 u/kg. In another embodiment, the amount is 1-1.2 u/kg. In another embodiment, the amount is 1-1.5 u/kg. In another embodiment, the amount is 1-2.5 u/kg. In another embodiment, the amount is 1-3 u/kg. In another embodiment, the amount is 2-3 u/kg. In another embodiment, the amount is 1-5 u/kg. In another embodiment, the amount is 2-5 u/kg. In another embodiment, the amount is 3-5 u/kg.

In another embodiment, the amount of insulin is 0.1 u/kg. In another embodiment, the amount is 0.2 u/kg. In another embodiment, the amount is 0.3 u/kg. In another embodiment, the amount is 0.4 u/kg. In another embodiment, the amount is 0.5 u/kg. In another embodiment, the amount is 0.6 u/kg. In another embodiment, the amount is 0.8 u/kg. In another embodiment, the amount is 1 u/kg. In another embodiment, the amount is 1.2 u/kg. In another embodiment, the amount is 1.4 u/kg. In another embodiment, the amount is 1.6 u/kg. In another embodiment, the amount is 1.8 u/kg. In another embodiment, the amount is 2 u/kg. In another embodiment, the amount is 2.2 u/kg. In another embodiment, the amount is 2.5 u/kg. In another embodiment, the amount is 3 u/kg.

In another embodiment, the amount of insulin is 1-10 u. In another embodiment, the amount is 2-10 u. In another embodiment, the amount is 3-10 u. In another embodiment, the amount is 5-10 u. In another embodiment, the amount is 1-20 u. In another embodiment, the amount is 2-20 u. In another embodiment, the amount is 3-20 u. In another embodiment, the amount is 5-20 u. In another embodiment, the amount is 7-20 u. In another embodiment, the amount is 10-20 u. In another embodiment, the amount is 12-20 u. In another embodiment, the amount is 10-12 u. In another embodiment, the amount is 10-15 u. In another embodiment, the amount is 10-25 u. In another embodiment, the amount is 10-30 u. In another embodiment, the amount is 20-30 u. In another embodiment, the amount is 10-50 u. In another embodiment, the amount is 20-50 u. In another embodiment, the amount is 30-50 u. In another embodiment, the amount is 20-100 u. In another embodiment, the amount is 30-100 u. In another embodiment, the amount is 100-150 u. In another embodiment, the amount is 100-250 u. In another embodiment, the amount is 100-300 u. In another embodiment, the amount is 200-300 u. In another embodiment, the amount is 100-500 u. In another embodiment, the amount is 200-500 u. In another embodiment, the amount is 300-500 u. In another embodiment, the amount is 200-1000 u. In another embodiment, the amount is 300-1000 u.

In another embodiment, the amount of insulin is 1 u. In another embodiment, the amount is 2 u. In another embodiment, the amount is 3 u. In another embodiment, the amount is 4 u. In another embodiment, the amount is 5 u. In another embodiment, the amount is 6 u. In another embodiment, the amount is 8 u. In another embodiment, the amount is 10 u. In another embodiment, the amount is 12 u. In another embodiment, the amount is 14 u. In another embodiment, the amount is 16 u. In another embodiment, the amount is 18 u. In another embodiment, the amount is 20 u. In another embodiment, the amount is 22 u. In another embodiment, the amount is 25 u. In another embodiment, the amount is 30 u. In another embodiment, the amount is 50 u. In another embodiment, the amount is 80 u. In another embodiment, the amount is 100 u. In another embodiment, the amount is 120 u. In another embodiment, the amount is 140 u. In another embodiment, the amount is 160 u. In another embodiment, the amount is 180 u. In another embodiment, the amount is 200 u. In another embodiment, the amount is 300 u. In another embodiment, the amount is 500 u.

In another embodiment, the protein is an insulin secretagogue. In another embodiment, the protein is GLP-1. In another embodiment, the protein is a GLP-1 analogue. In another embodiment, the protein is a GLP-1 mimetic. In another embodiment, the protein is an incretin mimetic. In another embodiment, the protein mimics the GLP-1 incretin. In another embodiment, the protein is GLP-2. In another embodiment, the protein is a GLP-2 analogue. In another embodiment, the protein is a GLP-2 mimetic.

In another embodiment, the protein is Exenatide. In another embodiment, the oral formulations of the present invention protect Exenatide breakdown in the stomach. In another embodiment, Exenatide formulation of the invention controls blood sugar levels. In another embodiment, Exenatide formulation of the invention helps control blood sugar levels. In another embodiment, Exenatide formulation of the invention induces pancreatic production of insulin. In another embodiment, Exenatide formulation of the invention is used to treat type-2 (non-insulin dependent) diabetes. In another embodiment, Exenatide formulation of the invention is used in conjunction with other diabetes medicines.

In another embodiment, the amount of Exenatide in a formulation as described herein is 10 mcg to 1 mg. In another embodiment, the amount of Exenatide in a formulation as described herein is 10 mcg to 25 mcg. In another embodiment, the amount of Exenatide in a formulation as described herein is 25 mcg to 50 mcg. In another embodiment, the amount of Exenatide in a formulation as described herein is 50 mcg to 60 mcg. In another embodiment, the amount of Exenatide in a formulation as described herein is 60 mcg to 70 mcg. In another embodiment, the amount of Exenatide in a formulation as described herein is 70 mcg to 80 mcg. In another embodiment, the amount of Exenatide in a formulation as described herein is 80 mcg to 90 mcg. In another embodiment, the amount of Exenatide in a formulation as described herein is 90 mcg to 100 mcg. In another embodiment, the amount of Exenatide in a formulation as described herein is 100 mcg to 110 mcg. In another embodiment, the amount of Exenatide in a formulation as described herein is 110 mcg to 125 mcg. In another embodiment, the amount of Exenatide in a formulation as described herein is 125 mcg to 150 mcg. In another embodiment, the amount of Exenatide in a formulation as described herein is 150 mcg to 175 mcg. In another embodiment, the amount of Exenatide in a formulation as described herein is 175 mcg to 200 mcg. In another embodiment, the amount of Exenatide in a formulation as described herein is 200 mcg to 220 mcg. In another embodiment, the amount of Exenatide in a formulation as described herein is 220 mcg to 240 mcg. In another embodiment, the amount of Exenatide in a formulation as described herein is 240 mcg to 260 mcg. In another embodiment, the amount of Exenatide in a formulation as described herein is 260 mcg to 300 mcg.

In another embodiment, the amount of Exenatide in a formulation as described herein is 300 mcg to 350 mcg. In another embodiment, the amount of Exenatide in a formulation as described herein is 350 mcg to 400 mcg. In another embodiment, the amount of Exenatide in a formulation as described herein is 400 mcg to 450 mcg. In another embodiment, the amount of Exenatide in a formulation as described herein is 450 mcg to 500 mcg. In another embodiment, the amount of Exenatide in a formulation as described herein is 550 mcg to 600 mcg. In another embodiment, the amount of Exenatide in a formulation as described herein is 600 mcg to 700 mcg. In another embodiment, the amount of Exenatide in a formulation as described herein is 700 mcg to 800 mcg. In another embodiment, the amount of Exenatide in a formulation as described herein is 800 mcg to 900 mcg. In another embodiment, the amount of Exenatide in a formulation as described herein is 900 mcg to 1 mg.

In another embodiment, the Exenatide formulation as described herein is taken twice a week. In another embodiment, the Exenatide formulation as described herein is taken once every two days. In another embodiment, the Exenatide formulation as described herein is taken once a day. In another embodiment, the Exenatide formulation as described herein is taken twice a day. In another embodiment, the Exenatide formulation as described herein is taken three times a day. In another embodiment, the Exenatide formulation as described herein is taken four times a day. In another embodiment, the Exenatide formulation as described herein is taken five times a day. In another embodiment, one of skill in the art determines the dosage of a Exenatide formulation as described herein. In another embodiment, one of skill in the art determines the daily dose of a Exenatide formulation as described herein. In another embodiment, one of skill in the art determines the daily dosing regimen of a Exenatide formulation as described herein.

In another embodiment, the Exenatide formulation as described herein is taken at least 15 minutes before a meal. In another embodiment, the Exenatide formulation as described herein is taken at least 30 minutes before a meal. In another embodiment, the Exenatide formulation as described herein is taken at least 45 minutes before a meal. In another embodiment, the Exenatide formulation as described herein is taken at least 60 minutes before a meal. In another embodiment, the Exenatide formulation as described herein is taken at least 75 minutes before a meal. In another embodiment, the Exenatide formulation as described herein is taken at least 90 minutes before a meal. In another embodiment, the Exenatide formulation as described herein is taken at least 100 minutes before a meal. In another embodiment, the Exenatide formulation as described herein is taken at least 120 minutes before a meal. In another embodiment, the Exenatide formulation as described herein is taken at least 150 minutes before a meal. In another embodiment, the Exenatide formulation as described herein is taken at least 180 minutes before a meal.

In another embodiment, the Exenatide formulation as described herein reduces the side effects associated with an injectable dosage form comprising Exenatide. In another embodiment, the Exenatide formulation as described herein reduces nausea as a side effect which is associated with an injectable dosage form comprising Exenatide. In another embodiment, the Exenatide formulation as described herein does not induce nausea as a side effect which is associated with an injectable dosage form comprising Exenatide.

In another embodiment, the protein is glucagon. In another embodiment, the protein is interferon gamma. In another embodiment, the protein is interferon alpha. In another embodiment, the protein is a growth hormone. In another embodiment, the protein is erythropoietin. In another embodiment, the protein is granulocyte colony stimulating factor (G-CSF). In another embodiment, the protein is omentin. In another embodiment, the protein is calcitonin. In another embodiment, the protein is PTH. In another embodiment, the protein is PYY.

In another embodiment, the protein is any other protein known in the art. In another embodiment, the protein is a growth hormone. In one embodiment, the growth hormone is somatotropin. In another embodiment, the growth hormone is Insulin Growth Factor-I (IGF-I). In another embodiment, the growth hormone is any other growth hormone known in the art.

In another embodiment, methods and compositions of the present invention are used to administer a human serum albumin. Human serum albumin is not, in one embodiment, considered to be a pharmaceutically-active component; however, it can be used in the context of the present invention as a therapeutically-beneficial carrier for an active component. Each type of protein represents a separate embodiment of the present invention.

In one embodiment, the protein is an enzyme. In some embodiments, the protein is a receptor ligand, transporter, or a storage protein. In one embodiment, the protein is a structural protein.

In some embodiments, the enzyme is an oxidoreductase, transferase, hydrolase, lyase, isomerase, or ligase. In some embodiments, oxidoreductases act on the aldehyde or oxo group of donors, on the CH—CH group of donors, on the CH—NH(2) group of donors, on the CH—NH group of donors, on NADH or NADPH, on the CH—OH group of donors, on nitrogenous compounds as donors, on a sulfur group of donors, on a heme group of donors, on diphenols and related substances as donors, on a peroxide as acceptor, on hydrogen as donor, on single donors with incorporation of molecular oxygen, on paired donors, on superoxide as acceptor, oxidizing metal ions, on CH or CH(2) groups, on iron-sulfur proteins as donors, on reduced flavodoxin as donor, on phosphorus or arsenic in donors, or on x-H and y-H to form an x-y bond.

In some embodiments, transferases are acyltransferases or glycosyltransferases. In some embodiments, transferases transfer aldehyde or ketone residues. In some embodiments, transferases transfer alkyl or aryl groups, other than methyl groups. In some embodiments, transferases transfer nitrogenous, phosphorous, sulfur or selenium containing groups.

In some embodiments, hydrolases are glycosylases or act on ether bonds, on peptide bonds, on carbon-nitrogen bonds, other than peptide bonds, on acid anhydrides, on carbon-carbon bonds, on halide bonds, on phosphorus-nitrogen bonds, on sulfur-nitrogen bonds, on carbon-phosphorus bonds, on sulfur-sulfur bonds, or on carbon-sulfur bonds.

In some embodiments, lyases are carbon-carbon lyases, carbon-oxygen lyases, carbon-nitrogen lyases, carbon-sulfur lyases, carbon-halide lyases, phosphorus-oxygen lyases, or other lyases.

In some embodiments, isomerases are racemases or epimerases, cis-trans-isomerases, intramolecular oxidoreductases, intramolecular transferases, intramolecular lyases, or other isomerases.

In some embodiments, ligases form carbon-sulfur bonds, carbon-nitrogen bonds, carbon-carbon bonds, phosphoric ester bonds, or nitrogen-metal bonds.

In some embodiments, transporter proteins are annexins, ATP-binding cassette transporters, hemoglobin, ATPases, calcium channels, potassium channels, sodium channels, or solute carriers.

In some embodiments, storage proteins comprise albumins, lactoglobulins, casein ovomucin, ferritin, phosvitin, lactoferrin, or vitellogenin. In one embodiment, albumins comprise avidin, ovalbumin, serum albumin, parvalbumin, c-reactive proteinprealbumin, conalbumin, ricin, lactalbumin, methemalbumin, or transthyretin.

In some embodiments, structural proteins comprise amyloid, collagen elastin, or fibrillin.

In some embodiments, the protein is a viral protein, bacterial protein, invertebrate protein, or vertebrate protein. In some embodiments, the protein is a recombinant protein. In one embodiment, the protein is a recombinant protein. In one embodiment, the recombinant protein is a recombinant human protein.

The molecular weights of some of the proteins mentioned above are as follows: insulin—6 kilodalton (kDa); glucagon—3.5 kDa; interferon, 28 kDa, growth hormone—21.5-47 kDa; human serum albumin—69 kDa; erythropoietin—34 kDa; G-CSF—30-34 kDa. Thus, in one embodiment, the molecular weight of these proteins is appropriate for administration by methods of the present invention.

As provided herein, a protease inhibitor protects the protein of the present invention from cleavage. In another embodiment, the present invention provides that a protease inhibitor protects insulin of the present invention from cleavage. In another, embodiment, the present invention provides that a protease inhibitor facilitates the protein absorption in the intestine of a subject. In another, embodiment, the present invention provides that a protease inhibitor facilitates the absorption of insulin in the intestine of a subject.

In another, embodiment, a serpin is: Alpha 1-antitrypsin, Antitrypsin-related protein, Alpha 1-antichymotrypsin, Kallistatin, Protein C inhibitor, Cortisol binding globulin, Thyroxine-binding globulin, Angiotensinogen, Centerin, Protein Z-related protease inhibitor, Vaspin, Monocyte neutrophil elastase inhibitor, Plasminogen activator inhibitor-2, Squamous cell carcinoma antigen-1 (SCCA-1), Squamous cell carcinoma antigen-2 (SCCA-2), Maspin, PI-6, Megsin, PI-8, PI-9, Bomapin, Yukopin, Hurpin/Headpin, Antithrombin, Heparin cofactor II, Plasminogen activator inhibitor 1, Glia derived nexin/Protease nexin I, Pigment epithelium derived factor, Alpha 2-antiplasmin, Complement 1-inhibitor, 47 kDa Heat shock protein (HSP47), Neuroserpin, or Pancpin.

In another embodiment, the present invention provides that the protease inhibitor is a trypsin inhibitor such as but not limited to: Lima bean trypsin inhibitor, Aprotinin, soy bean trypsin inhibitor (SBTI), or Ovomucoid.

In another embodiment, the present invention provides that the protease inhibitor is a Cysteine protease inhibitor. In another, embodiment, the present invention provides that Cysteine protease inhibitors of the invention comprise: cystatin, type 1 cystatins (or stefins), Cystatins of type 2,human cystatins C, D, S, SN, and SA, cystatin E/M, cystatin F, type 3 cystatins, or kininogens.

In another embodiment, the present invention provides that the protease inhibitor is a Threonine protease inhibitor. In another, embodiment, the present invention provides that Threonine protease inhibitors of the invention comprise: Bortezomib, MLN-519, ER-807446, TMC-95A.

In another embodiment, the present invention provides that the protease inhibitor is an Aspartic protease inhibitor. In another, embodiment, the present invention provides that Aspartic protease inhibitors of the invention comprise: $\alpha_2$-Macroglobulin, Pepstatin A, Aspartic protease inhibitor 11, Aspartic protease inhibitor 1, Aspartic protease inhibitor 2, Aspartic protease inhibitor 3, Aspartic protease inhibitor 4, Aspartic protease inhibitor 5, Aspartic protease inhibitor 6, Aspartic protease inhibitor 7, Aspartic protease inhibitor 8, Aspartic protease inhibitor 9, Pepsin inhibitor Dit33, Aspartyl protease inhibitor, or Protease A inhibitor 3.

In another embodiment, the present invention provides that the protease inhibitor is a Metalloprotease inhibitor. In another, embodiment, the present invention provides that Metalloprotease inhibitors of the invention comprise: Angiotensin-1-converting enzyme inhibitory peptide, Antihemorragic factor BJ46a, Beta-casein, Proteinase inhibitor CeKI, Venom metalloproteinase inhibitor DM43, Carboxypeptidase A inhibitor, smpI, IMPI, Alkaline proteinase, inh, Latexin, Carboxypeptidase inhibitor, Antihemorragic factor HSF, Testican-3, SPOCK3, TIMP1, Metalloproteinase inhibitor 1, Metalloproteinase inhibitor 2, TIMP2, Metalloproteinase inhibitor 3, TIMP3, Metalloproteinase inhibitor 4, TIMP4, Putative metalloproteinase inhibitor tag-225, Tissue inhibitor of metalloprotease, WAP, kazal, immunoglobulin, or kunitz and NTR domain-containing protein 1.

In some embodiments, a protease inhibitor is a suicide inhibitor, a transition state inhibitor, or a chelating agent. In some embodiments, the protease inhibitor of the present invention is: AEBSF-HCl, (epsilon)-aminocaproic acid, (alpha) 1-antichymotypsin, antipain, antithrombin III, (alpha) 1-antitrypsin ([alpha] 1-proteinase inhibitor), APMSF-HCl (4-amidinophenyl-methane sulfonyl-fluoride), sprotinin, benzamidine-HCl,chymostatin, DFP (diisopropylfluorophosphate), leupeptin, PEFABLOC® SC (4-(2-Aminoethyl)-benzenesulfonyl fluoride hydrochloride), PMSF (phenylmethyl sulfonyl fluoride), TLCK (1-Chloro-3-tosylamido-7-amino-2-heptanone HCl), TPCK (1-Chloro-3-tosylamido-4-phenyl-2-butanone), pentamidine isethionate, pepstatin, guanidium, alpha2-macroglobulin, a chelating agent of zinc, or iodoacetate, zinc. Each possibility represents a separate embodiment of the present invention.

In another embodiment, the amount of a protease inhibitor utilized in methods and compositions of the present invention is 0.1 mg/dosage unit. In another embodiment, the amount of a protease inhibitor is 0.2 mg/dosage unit. In another embodiment, the amount is 0.3 mg/dosage unit. In another embodiment, the amount is 0.4 mg/dosage unit. In another embodiment, the amount is 0.6 mg/dosage unit. In another embodiment, the amount is 0.8 mg/dosage unit. In another embodiment, the amount is 1 mg/dosage unit. In another embodiment, the amount is 1.5 mg/dosage unit. In another embodiment, the amount is 2 mg/dosage unit. In another embodiment, the amount is 2.5 mg/dosage unit. In another embodiment, the amount is 3 mg/dosage unit. In another embodiment, the amount is 5 mg/dosage unit. In another embodiment, the amount is 7 mg/dosage unit. In another embodiment, the amount is 10 mg/dosage unit. In another embodiment, the amount is 12 mg/dosage unit. In another embodiment, the amount is 15 mg/dosage unit. In another embodiment, the amount is 20 mg/dosage unit. In another embodiment, the amount is 30 mg/dosage unit. In another embodiment, the amount is 50 mg/dosage unit. In another embodiment, the amount is 70 mg/dosage unit. In another embodiment, the amount is 100 mg/dosage unit.

In another embodiment, the amount of a protease inhibitor is 0.1-1 mg/dosage unit. In another embodiment, the amount of a protease inhibitor is 0.2-1 mg/dosage unit. In another embodiment, the amount is 0.3-1 mg/dosage unit. In another embodiment, the amount is 0.5-1 mg/dosage unit. In another embodiment, the amount is 0.1-2 mg/dosage unit. In another embodiment, the amount is 0.2-2 mg/dosage unit. In another embodiment, the amount is 0.3-2 mg/dosage unit. In another embodiment, the amount is 0.5-2 mg/dosage unit. In another embodiment, the amount is 1-2 mg/dosage unit. In another embodiment, the amount is 1-10 mg/dosage unit. In another embodiment, the amount is 2-10 mg/dosage unit. In another embodiment, the amount is 3-10 mg/dosage unit. In another embodiment, the amount is 5-10 mg/dosage unit. In another embodiment, the amount is 1-20 mg/dosage unit. In another embodiment, the amount is 2-20 mg/dosage unit. In another embodiment, the amount is 3-20 mg/dosage unit. In another embodiment, the amount is 5-20 mg/dosage unit. In another embodiment, the amount is 10-20 mg/dosage unit. In another embodiment, the amount is 10-100 mg/dosage unit. In another embodiment, the amount is 20-100 mg/dosage unit. In another embodiment, the amount is 30-100 mg/dosage unit. In another embodiment, the amount is 50-100 mg/dosage unit. In another embodiment, the amount is 10-200 mg/dosage unit. In another embodiment, the amount is 20-200 mg/dosage unit. In another embodiment, the amount is 30-200 mg/dosage unit. In another embodiment, the amount is 50-200 mg/dosage unit. In another embodiment, the amount is 100-200 mg/dosage unit.

In another embodiment, the amount of a protease inhibitor utilized in the methods and compositions of the present invention is 1000 k.i.u. (kallikrein inactivator units)/ dosage unit. In another embodiment, the amount is 10 k.i.u./dosage unit. In another embodiment, the amount is 12 k.i.u./dosage unit. In another embodiment, the amount is 15 k.i.u./dosage unit. In another embodiment, the amount is 20 k.i.u./dosage unit. In another embodiment, the amount is 30 k.i.u./dosage unit. In another embodiment, the amount is 40 k.i.u./dosage unit. In another embodiment, the amount is 50 k.i.u./dosage unit. In another embodiment, the amount is 70 k.i.u./dosage unit. In another embodiment, the amount is 100 k.i.u./dosage unit. In another embodiment, the amount is 150 k.i.u./dosage unit. In another embodiment, the amount is 200 k.i.u./dosage unit. In another embodiment, the amount is 300 k.i.u./dosage unit. In another embodiment, the amount is 500 k.i.u./dosage unit. In another embodiment, the amount is 700 k.i.u./dosage unit. In another embodiment, the amount is 1500 k.i.u./dosage unit. In another embodiment, the amount is 3000 k.i.u./dosage unit. In another embodiment, the amount is 4000 k.i.u./dosage unit. In another embodiment, the amount is 5000 k.i.u./dosage unit. Each amount of a first or a second protease inhibitor represents a separate embodiment of the present invention.

In another embodiment, the amount is 50-5000 k.i.u./dosage unit. In another embodiment, the amount is 500-4000 k.i.u./dosage unit. In another embodiment, the amount is 100-1000 k.i.u./dosage unit. In another embodiment, the amount is 200-1500 k.i.u./dosage unit.

In another embodiment, compositions of the present invention comprise a substance that enhances absorption of a protein of the invention through an intestinal mucosal barrier. In another embodiment, compositions of the present invention further comprise a substance that enhances absorption of insulin through an intestinal mucosal barrier. In another embodiment, compositions of the present invention further comprise a substance that enhances absorption of Exenatide through an intestinal mucosal barrier. In another embodiment, compositions of the present invention further comprise a substance that reduces the degradation of Exenatide in the digestive system. In another embodiment, compositions of the present invention further comprise a substance that reduces the degradation of Exenatide in the stomach. In another embodiment, compositions of the present invention further comprise a substance that reduces the degradation of Exenatide in the intestine. Such a substance is referred to herein as an "enhancer." As provided herein, enhancers, when used together with omega-3 fatty acids or a protease inhibitor, enhance the ability of a proitein to be absorbed in the intestine. As provided herein, enhancers, when used together with omega-3 fatty acids and a protease inhibitor, enhance the ability of insulin to be absorbed in the intestine. As provided herein, enhancers, when used together with omega-3 fatty acids and a protease inhibitor, enhance the ability of Exenatide to be absorbed in the intestine.

In one embodiment, the enhancer is didecanoylphosphatidylcholine (DDPC). In one embodiment, the enhancer is a chelating agent such as ethylenediaminetetraacetic acid (EDTA) or egtazic acid EGTA. In another embodiment, EDTA is sodium-EDTA. In some embodiments, the enhancer is NO donor. In some embodiments, the enhancer is a bile acid, glycine-conjugated form of a bile acid, or an alkali metal salt. In one embodiment, absorption enhancement is achieved through utilization of a combination of α-galactosidase and β-mannanase. In some embodiments, the enhancer is a fatty acid such as sodium caprate. In one embodiment, the enhancer is sodium glycocholate. In one embodiment, the enhancer is sodium salicylate. In one embodiment, the enhancer is n-dodecyl-β-D-maltopyranoside. In some embodiments, surfactants serve as absorption enhancer. In one embodiment, the enhancer is chitisan such as N,N,N-trimethyl chitosan chloride (TMC).

In one embodiment, NO donors of the present invention comprise 3-(2-Hydroxy-1-(1-methylethyl)-2-nitrosohydrazino)-1-propanamine, N-ethyl-2-(1-ethyl-hydroxy-2-nitrosohydrazino)-ethanamine, or S-Nitroso-N-acetylpenicillamine In another embodiment, the bile acid is cholic acid. In another embodiment, the bile acid is chenodeoxycholic acid. In another embodiment, the bile acid is taurocholic acid. In another embodiment, the bile acid is taurochenodeoxycholic acid. In another embodiment, the bile acid is glycocholic acid. In another embodiment, the bile acid is glycochenocholic acid. In another embodiment, the bile acid is 3 beta-monohydroxychloric acid. In another embodiment, the bile acid is lithocholic acid. In another embodiment, the bile acid is 5 beta-cholanic acid. In another embodiment, the bile acid is 3,12-diol-7-one-5 beta-cholanic acid. In another embodiment, the bile acid is 3 alpha-hydroxy-12-ketocholic acid. In another embodiment, the bile acid is 3 beta-hydroxy-12-ketocholic acid. In another embodiment, the bile acid is 12 alpha-3 beta-dihydrocholic acid. In another embodiment, the bile acid is ursodesoxycholic acid.

In one embodiment, the enhancer is a nonionic surfactant. In one embodiment, the enhancer is a nonionic polyoxyethylene ether surface active agent (e.g one having an HLB value of 6 to 19, wherein the average number of polyoxyethylene units is 4 to 30). In another embodiment, the enhancer is an anionic surface active agents. In another embodiment, the enhancer is a cationic surface active agent. In another embodiment, the enhancer is an ampholytic surface active agent. In one embodiment, zwitteruionic surfactants such as acylcarnitines serve as absorption enhancers.

In another embodiment, the absorption enhancer is an effective oral absorption enhancer for macromolecular drugs. In another embodiment, the absorption enhancer is very water soluble. In another embodiment, the absorption enhancer is fully, i. e. greater than 85%, absorbed by the gastro-intestinal tract. In another embodiment, the absorption enhancer is a coarse form. In another embodiment, the absorption enhancer is micronized. In another embodiment, the absorption enhancer is amorphous. In another embodiment, the absorption enhancer is N-(5-chlorosalicyloyl)-8-aminocaprylic acid (5-CNAC). In another embodiment, the absorption enhancer is N-(10[2-hydroxybenzoyl]amino)decanoic acid (SNAD). In another embodiment, the absorption enhancer is N-(8-[2-hydroxybenzoyl]amino) caprylic acid (SNAC). In another embodiment, the absorption enhancer is CNAC, SNAD, SNAC, a monosodium and/or disodium salts thereof, ethanol solvates of sodium salts thereof and the monohydrates of sodium salts thereof and any combinations thereof. In another embodiment, the absorption enhancer is 8-(N-2-hydroxy-4-methoxybenzoyl)-aminocaprylic acid (4-MOAC) and pharmaceutically acceptable salts thereof and/or amorphous and polymorphic forms of 4-MOAC. In another embodiment, the absorption enhancer is N-(8-[2-hydroxy-5-chlorobenzoyl]-amino)octanoic acid (also known as 8-(N-2-hydroxy-5-chlorobenzoyl)aminocaprylic acid)) (5-CNAC) and pharmaceutically acceptable salts thereof and/or amorphous and polymorphic forms of 5-CNAC. In another embodiment, the absorption enhancer is 4-[(2-hydroxy-4-chlorobenzoyl) amino]butanoate (also known as 4-[(4-chloro-2-hydroxybenzoyl)amino]butanoic acid) (4-CNAB) and pharmaceutically acceptable salts thereof, including its monosodium salt and/or amorphous and polymorphic forms of 4-CNAB.

In another embodiment, there is a synergistic effect in lowering blood glucose level of SNAD and a protease inhibitor of the invention. In another embodiment, there is a synergistic effect in lowering blood glucose level of SNAC and a protease inhibitor of the invention.

In another embodiment, the pharmaceutical compositions of the present invention comprise a delivery effective amount of one or more of the absorption enhancers. In another embodiment, the pharmaceutical compositions of the present invention comprise an amount sufficient to deliver the active agent for the desired effect.

In another embodiment, the pharmaceutical compositions of the present invention comprise an amount of 2.5% to 99.4% by weight of an absorption enhancer. In another embodiment, the pharmaceutical compositions of the present invention comprise an amount of 2.5% to 10% by weight of a absorption enhancer. In another embodiment, the pharmaceutical compositions of the present invention comprise an amount of 8% to 15% by weight of a absorption enhancer. In another embodiment, the pharmaceutical compositions of the present invention comprise an amount of 10% to 20% by weight of a absorption enhancer. In another embodiment, the pharmaceutical compositions of the present invention comprise an amount of 15% to 30% by weight of an absorption enhancer. In another embodiment, the pharmaceutical compositions of the present invention comprise an amount of 20% to 40% by weight of an absorption enhancer. In another embodiment, the pharmaceutical compositions of the present invention comprise an amount of 30% to 50% by weight of an absorption enhancer. In another embodiment, the pharmaceutical compositions of the present invention comprise an amount of 40% to 60% by weight of an absorption enhancer. In another embodiment, the pharmaceutical compositions of the present invention comprise an amount of 50% to 70% by weight of an absorption enhancer. In another embodiment, the pharmaceutical compositions of the present invention comprise an amount of 70% to 99.4% by weight of an absorption enhancer. In another embodiment, the amount of an absorption enhancer in the present composition is a delivery effective amount and can be determined for any particular carrier or biologically or chemically active agent by methods known to those skilled in the art.

In another embodiment, an absorption enhancer is a peptide. In another embodiment, an absorption enhancer is an amino acid. In another embodiment, a absorption enhancer is derived from amino acids.

In another embodiment, the amount of enhancer utilized in methods and compositions of the present invention is 0.1 mg/dosage unit. In another embodiment, the amount of enhancer is 0.2 mg/dosage unit. In another embodiment, the amount is 0.3 mg/dosage unit. In another embodiment, the amount is 0.4 mg/dosage unit. In another embodiment, the amount is 0.6 mg/dosage unit. In another embodiment, the amount is 0.8 mg/dosage unit. In another embodiment, the amount is 1 mg/dosage unit. In another embodiment, the amount is 1.5 mg/dosage unit. In another embodiment, the amount is 2 mg/dosage unit. In another embodiment, the amount is 2.5 mg/dosage unit. In another embodiment, the amount is 3 mg/dosage unit. In another embodiment, the amount is 5 mg/dosage unit. In another embodiment, the amount is 7 mg/dosage unit. In another embodiment, the amount is 10 mg/dosage unit. In another embodiment, the amount is 12 mg/dosage unit. In another embodiment, the amount is 15 mg/dosage unit. In another embodiment, the amount is 20 mg/dosage unit. In another embodiment, the amount is 30 mg/dosage unit. In another embodiment, the amount is 50 mg/dosage unit. In another embodiment, the amount is 70 mg/dosage unit. In another embodiment, the amount is 100 mg/dosage unit.

In another embodiment, the amount of enhancer is 0.1-1 mg/dosage unit. In another embodiment, the amount of enhancer is 0.2-1 mg/dosage unit. In another embodiment, the amount is 0.3-1 mg/dosage unit. In another embodiment, the amount is 0.5-1 mg/dosage unit. In another embodiment, the amount is 0.1-2 mg/dosage unit. In another embodiment, the amount is 0.2-2 mg/dosage unit. In another embodiment, the amount is 0.3-2 mg/dosage unit. In another embodiment, the amount is 0.5-2 mg/dosage unit. In another embodiment, the amount is 1-2 mg/dosage unit. In another embodiment, the amount is 1-10 mg/dosage unit. In another embodiment, the amount is 2-10 mg/dosage unit. In another embodiment, the amount is 3-10 mg/dosage unit. In another embodiment, the amount is 5-10 mg/dosage unit. In another embodiment, the amount is 1-20 mg/dosage unit. In another embodiment, the amount is 2-20 mg/dosage unit. In another embodiment, the amount is 3-20 mg/dosage unit. In another embodiment, the amount is 5-20 mg/dosage unit. In another embodiment, the amount is 10-20 mg/dosage unit. In another embodiment, the amount is 10-100 mg/dosage unit. In another embodiment, the amount is 20-100 mg/dosage unit. In another embodiment, the amount is 30-100 mg/dosage unit. In another embodiment, the amount is 50-100 mg/dosage unit. In another embodiment, the amount is 10-200 mg/dosage unit. In another embodiment, the amount is 20-200 mg/dosage unit. In another embodiment, the amount is 30-200 mg/dosage unit. In another embodiment, the amount is 50-200 mg/dosage unit. In another embodiment, the amount is 100-200 mg/dosage unit. Each type and amount of enhancer represents a separate embodiment of the present invention.

In some embodiments, omega-3 fatty acid can be found in vegetable sources such as the seeds of chia, perilla, flax, walnuts, purslane, lingonberry, seabuckthorn, and hemp. In some embodiments, omega-3 fatty acids can also be found in the fruit of the acai palm. In another embodiment, the omega-3 fatty acid has been provided in the form of a synthetic omega-3 fatty acid. In one embodiment, the omega-3 fatty acid of methods and compositions of the present invention has been provided to the composition in the form of fish oil. In another embodiment, the omega-3 fatty acid has been provided in the form of canola oil. In another embodiment, the omega-3 fatty acid has been provided in the form of flaxseed oil. In another embodiment, the omega-3 fatty acid has been provided in the form of any other omega-3 fatty acid-rich source known in the art. In another embodiment, the omega-3 fatty acid has been provided in the form of a synthetic omega-3 fatty acid. Each form of omega-3 fatty acids represents a separate embodiment of the present invention.

In another embodiment, the omega-3 fatty acid of methods and compositions of the present invention is an omega-3 polyunsaturated fatty acid. In another embodiment, the omega-3 fatty acid is DHA, an omega-3, polyunsaturated, 22-carbon fatty acid also referred to as 4,7,10,13,16,19-docosahexaenoic acid. In another embodiment, the omega-3 fatty acid is -linolenic acid (9,12,15-octadecatrienoic acid). In another embodiment, the omega-3 fatty acid is stearidonic acid (6,9,12,15-octadecatetraenoic acid). In another embodiment, the omega-3 fatty acid is eicosatrienoic acid (ETA; 11,14,17-eicosatrienoic acid). In another embodiment, the omega-3 fatty acid is eicsoatetraenoic acid (8,11,14,17-eicosatetraenoic acid). In one embodiment, the omega-3 fatty acid is eicosapentaenoic acid (EPA; 5,8,11,14,17-eicosapentaenoic acid). In another embodiment, the omega-3 fatty acid is eicosahexaenoic acid (also referred to as "EPA"; 5,7,9,11,14,17-eicosahexaenoic acid). In another embodiment, the omega-3 fatty acid is docosapentaenoic acid (DPA; 7,10,13,16,19-docosapenatenoic acid). In another embodiment, the omega-3 fatty acid is tetracosahexaenoic acid (6,9,12,15,18,21-tetracosahexaenoic acid). In another embodiment, the omega-3 fatty acid is any other omega-3 fatty acid known in the art. Each omega-3 fatty acid represents a separate embodiment of the present invention.

In another embodiment, compositions of the present invention further comprise a coating that inhibits digestion of the composition in a subject's stomach. In one embodiment, coating inhibits digestion of the composition in a subject's stomach. In one embodiment, the coated dosage forms of the present invention release drug when pH move towards alkaline range. In one embodiment, coating is a monolayer, wherein in other embodiments coating applied in multilayers. In one embodiment, coating is a bioadhesive polymer that selectively binds the intestinal mucosa and thus enables drug release in the attachment site. In one embodiment, the enteric coating is an enteric film coating. In some embodiment, coating comprises biodegradable polysaccharide, chitosan, aquateric aqueous, aquacoat ECD, azo polymer, cellulose acetate phthalate, cellulose acetate trimelliate, hydroxypropylmethyl cellulose phthalate, gelatin, poly vinyl acetate phthalate, hydrogel, pulsincap, or a combination thereof. In one embodiment, pH sensitive coating will be used according to the desired release site and/or profile as known to one skilled in the art.

In one embodiment, the coating is an enteric coating. Methods for enteric coating are well known in the art, and are described, for example, in Siepmann F, Siepmann J et al, Blends of aqueous polymer dispersions used for pellet coating: importance of the particle size. J Control Release 2005; 105(3): 226-39; and Huyghebaert N, Vermeire A, Remon J P. In vitro evaluation of coating polymers for enteric coating and human ileal targeting. Int J Pharm 2005; 298(1): 26-37. Each method represents a separate embodiment of the present invention.

In another embodiment, Eudragit®, an acrylic polymer, is used as the enteric coating. The use of acrylic polymers for the coating of pharmaceutical preparations is well known in the art. Eudragit Acrylic Polymers have been shown to be safe, and are neither absorbed nor metabolized by the body, but rather are eliminated.

In another embodiment, the coating is a gelatin coating. In another embodiment, microencapsulation is used to protect the insulin against decomposition in the stomach. In another embodiment, the coating is a gelatin coating. In another embodiment, microencapsulation is used to protect Exenatide against decomposition in the stomach. Methods for applying a gelatin coating and for microencapsulation are well known in the art. Each method represents a separate embodiment of the present invention.

In another embodiment, the coating is a film-coating. In another embodiment, the coating is ethylcellulose. In another embodiment, the coating is a water-based dispersion of ethylcellulose, e.g. hydroxypropylmethylcelullose (HPMC) E15. In another embodiment, the coating is a gastro-resistant coating, e.g. a polymer containing carboxylic acid groups as a functional moiety. In another embodiment, the coating is a monolithic matrix. In another embodiment, the coating is cellulose ether (e.g. hypromellose (HPMC). Each type of coating represents a separate embodiment of the present invention.

In another embodiment, the present invention provides a composition comprising an active protein of the invention, a protease inhibitor, and an absorption enhancer. In another embodiment, the present invention provides a composition comprising an active protein of the invention, a protease inhibitor, an omega-3 fatty acid, and an absorption enhancer. In another embodiment, the present invention provides a composition comprising an active protein of the invention, a protease inhibitor, an omega-3 fatty acid, EDTA or Na-EDTA, and an absorption enhancer.

In another embodiment, the present invention provides that the use of at least one protease inhibitor and an absorption enhancer in a single oral composition dramatically, unexpectedly, increase the bioavailability of a protein of the invention. In another embodiment, the present invention provides that the use of at least one protease inhibitor and an absorption enhancer in a single oral composition dramatically, unexpectedly, increase the bioavailability of insulin. In another embodiment, the present invention provides that the use of at least one protease inhibitor and an absorption enhancer in a single oral composition dramatically, unexpectedly, increase the bioavailability of Exenatide.

In another embodiment, the present invention provides that the use of at least one protease inhibitor and an absorption enhancer in a single oral composition dramatically, unexpectedly, increase the bioavailability of a protein of the invention. In another embodiment, the present invention provides that the use of at least one protease inhibitor and an absorption enhancer in a single oral composition dramatically, unexpectedly, increase the bioavailability of insulin. In another embodiment, the present invention provides that the use of at least one protease inhibitor and an absorption enhancer in a single oral composition dramatically, unexpectedly, increase the bioavailability of Exenatide.

In another embodiment, the present invention provides that the use of at least one protease inhibitor and SNAC in a single oral composition dramatically, unexpectedly, increase the bioavailability of a protein of the invention. In another embodiment, the present invention provides that the use of at least one protease inhibitor and SNAC in a single oral composition dramatically, unexpectedly, increase the bioavailability of insulin. In another embodiment, the present invention provides that the use of at least one protease inhibitor and SNAC in a single oral composition dramatically, unexpectedly, increase the bioavailability of Exenatide.

In another embodiment, the present invention provides that the use of at least one protease inhibitor and SNAD in a single oral composition dramatically, unexpectedly, increase the bioavailability of a protein of the invention. In another embodiment, the present invention provides that the use of at least one protease inhibitor and SNAD in a single oral composition dramatically, unexpectedly, increase the bioavailability of insulin. In another embodiment, the present invention provides that the use of at least one protease inhibitor and SNAD in a single oral composition dramatically, unexpectedly, increase the bioavailability of Exenatide.

In another embodiment, the present invention provides that the use of a serpin and SNAC or SNAD in a single oral composition dramatically, unexpectedly, increase the bioavailability of a protein of the invention. In another embodiment, the present invention provides that the use of a serpin and SNAC or SNAD in a single oral composition dramatically, unexpectedly, increase the bioavailability of insulin. In another embodiment, the present invention provides that the use of a serpin and SNAC or SNAD in a single oral composition dramatically, unexpectedly, increase the bioavailability of Exenatide. In another embodiment, the present invention provides that the use of a serpin and SNAC or SNAD in a single oral composition dramatically, unexpectedly, increase the bioavailability of a protein of the invention.

In another embodiment, the present invention provides that the use of a trypsin inhibitor and SNAC or SNAD in a single oral composition dramatically, unexpectedly, increase the bioavailability of insulin. In another embodiment, the present invention provides that the use of a trypsin inhibitor and SNAC or SNAD in a single oral composition dramatically, unexpectedly, increase the bioavailability of Exenatide. In another embodiment, the present invention provides that the use of SBTI or Aprotinin and SNAC or SNAD in a single oral composition dramatically, unexpectedly, increase the bioavailability of a protein of the invention. In another embodiment, the present invention provides that the use of SBTI or Aprotinin and SNAC or SNAD in a single oral composition dramatically, unexpectedly, increase the bio availability of insulin. In another embodiment, the present invention provides that the use of SBTI or Aprotinin and SNAC or SNAD in a single oral composition dramatically, unexpectedly, increase the bio availability of Exenatide.

In another embodiment, the present invention provides that the use of a Cysteine protease inhibitor and SNAC or SNAD in a single oral composition dramatically, unexpectedly, increase the bioavailability of a protein of the invention. In another embodiment, the present invention provides that the use of a Cysteine protease inhibitor and SNAC or SNAD in a single oral composition dramatically, unexpectedly, increase the bioavailability of insulin. In another embodiment, the present invention provides that the use of a Cysteine protease inhibitor and SNAC or SNAD in a single oral composition dramatically, unexpectedly, increase the bioavailability of Exenatide.

In another embodiment, the present invention provides that the use of a Threonine protease inhibitor and SNAC or SNAD in a single oral composition dramatically, unexpectedly, increase the bio availability of a protein of the invention. In another embodiment, the present invention provides that the use of a Threonine protease inhibitor and SNAC or SNAD in a single oral composition dramatically, unexpectedly, increase the bioavailability of insulin. In another embodiment, the present invention provides that the use of a Threonine protease inhibitor and SNAC or SNAD in a single oral composition dramatically, unexpectedly, increase the bio availability of Exenatide.

In another embodiment, the present invention provides that the use of a Metalloprotease protease inhibitor and SNAC or SNAD in a single oral composition dramatically, unexpectedly, increase the bioavailability of a protein of the invention. In another embodiment, the present invention provides that the use of a Metalloprotease protease inhibitor and SNAC or SNAD in a single oral composition dramatically, unexpectedly, increase the bioavailability of insulin. In another embodiment, the present invention provides that the use of a Metalloprotease protease inhibitor and SNAC or SNAD in a single oral composition dramatically, unexpectedly, increase the bio availability of Exenatide.

In another embodiment, the present invention provides that the use of an Aspartic protease inhibitor and SNAC or SNAD in a single oral composition dramatically, unexpectedly, increase the bioavailability of a protein of the invention. In another embodiment, the present invention provides that the use of an Aspartic protease inhibitor and SNAC or SNAD in a single oral composition dramatically, unexpectedly, increase the bioavailability of insulin. In another embodiment, the present invention provides that the use of an Aspartic protease inhibitor and SNAC or SNAD in a single oral composition dramatically, unexpectedly, increase the bio-availability of Exenatide.

In another embodiment, the present invention provides that the use of a protease inhibitor and SNAC or SNAD in a single oral composition dramatically, unexpectedly, increase the bioavailability of insulin in a human subject by at least 10%. In another embodiment, the present invention provides that the use of a protease inhibitor and SNAC or SNAD in a single oral composition dramatically, unexpectedly, increase the bioavailability of Exenatide in a human subject by at least 10%. In another embodiment, the present invention provides that the use of a protease inhibitor and SNAC or SNAD in a single oral composition dramatically, unexpectedly, increase the bioavailability of insulin in a human subject by at least 20%. In another embodiment, the present invention provides that the use of a protease inhibitor and SNAC or SNAD in a single oral composition dramatically, unexpectedly, increase the bioavailability of Exenatide in a human subject by at least 20%. In another embodiment, the present invention provides that the use of a protease inhibitor and SNAC or SNAD in a single oral composition dramatically, unexpectedly, increase the bioavailability of insulin in a human subject by at least 30%. In another embodiment, the present invention provides that the use of a protease inhibitor and SNAC or SNAD in a single oral composition dramatically, unexpectedly, increase the bioavailability of Exenatide in a human subject by at least 30%. In another embodiment, the present invention provides that the use of a protease inhibitor and SNAC or SNAD in a single oral composition dramatically, unexpectedly, increase the bioavailability of insulin in a human subject by at least 40%. In another embodiment, the present invention provides that the use of a protease inhibitor and SNAC or SNAD in a single oral composition dramatically, unexpectedly, increase the bioavailability of Exenatide in a human subject by at least 40%. In another embodiment, the present invention provides that the use of a protease inhibitor and SNAC or SNAD in a single oral composition dramatically, unexpectedly, increase the bioavailability of insulin in a human subject by at least 50%. In another embodiment, the present invention provides that the use of a protease inhibitor and SNAC or SNAD in a single oral composition dramatically, unexpectedly, increase the bio availability of Exenatide in a human subject by at least 50%. In another embodiment, the present invention provides that the use of a protease inhibitor and SNAC or SNAD in a single oral composition dramatically, unexpectedly, increase the bioavailability of insulin in a human subject by at least 60%. In another embodiment, the present invention provides that the use of a protease inhibitor and SNAC or SNAD in a single oral composition dramatically, unexpectedly, increase the bioavailability of Exenatide in a human subject by at least 60%. In another embodiment, the present invention provides that the use of a protease inhibitor and SNAC or SNAD in a single oral composition dramatically, unexpectedly, increase the bioavailability of insulin in a human subject by at least 70%. In another embodiment, the present invention provides that the use of a protease inhibitor and SNAG or SNAD in a single oral composition dramatically, unexpectedly, increase the bioavailability of Exenatide in a human subject by at least 70%. In another embodiment, the present invention provides that the use of a protease inhibitor and SNAC or SNAD in a single oral composition dramatically, unexpectedly, increase the bioavailability of insulin in a human subject by at least 80%. In another embodiment, the present invention provides that the use of a protease inhibitor and SNAC or SNAD in a single oral composition dramatically, unexpectedly, increase the bioavailability of Exenatide in a human subject by at least 80%. In another embodiment, the present invention provides that the use of a protease inhibitor and SNAC or SNAD in a single oral composition dramatically, unexpectedly, increase the bioavailability of insulin in a human subject by at least 90%. In another embodiment, the present invention provides that the use of a protease inhibitor and SNAC or SNAD in a single oral composition dramatically, unexpectedly, increase the bioavailability of Exenatide in a human subject by at least 90%. In another embodiment, the present invention provides that the use of a protease inhibitor and SNAC or SNAD in a single oral composition dramatically, unexpectedly, increase the bioavailability of insulin in a human subject by at least 100%. In another embodiment, the present invention provides that the use of a protease inhibitor and SNAC or SNAD in a single oral composition dramatically, unexpectedly, increase the bioavailability of Exenatide in a human subject by at least 100%.

In another embodiment, the present invention provides that the use of Aprotinin or SBTI and SNAC or SNAD in a single oral composition dramatically, unexpectedly, increase the bioavailability of insulin in a human subject by at least 10%. In another embodiment, the present invention provides that the use of Aprotinin or SBTI and SNAC or SNAD in a single oral composition dramatically, unexpectedly, increase the bioavailability of insulin in a human subject by at least 20%. In another embodiment, the present invention provides that the use of Aprotinin or SBTI and SNAC or SNAD in a single oral composition dramatically, unexpectedly, increase the bioavailability of insulin in a human subject by at least 30%. In another embodiment, the present invention provides that the use of Aprotinin or SBTI and SNAC or SNAD in a single oral composition dramatically, unexpectedly, increase the bioavailability of insulin in a human subject by at least 40%. In another embodiment, the present invention provides that the use of Aprotinin or SBTI and SNAC or SNAD in a single oral composition dramatically, unexpectedly, increase the bioavailability of insulin in a human subject by at least 50%. In another embodiment, the present invention provides that the use of Aprotinin or SBTI and SNAC or SNAD in a single oral composition dramatically, unexpectedly, increase the bioavailability of insulin in a human subject by at least 60%. In another embodiment, the present invention provides that the use of Aprotinin or SBTI and SNAC or SNAD in a single oral composition dramatically, unexpectedly, increase the bioavailability of insulin in a human subject by at least 70%. In another embodiment, the present invention provides that the use of Aprotinin or SBTI and SNAG or SNAD in a single oral composition dramatically, unexpectedly, increase the bioavailability of insulin in a human subject by at least 80%. In another embodiment, the present invention provides that the use of Aprotinin or SBTI and SNAC or SNAD in a single oral composition dramatically, unexpectedly, increase the bioavailability of insulin in a human subject by at least 90%. In another embodiment, the present invention provides that the use of Aprotinin or SBTI and SNAC or SNAD in a single oral composition dramatically, unexpectedly, increase the bioavailability of insulin in a human subject by at least 100%.

In another embodiment, this invention further provides the use of sustained release dosage forms (e.g. sustained release microencapsulation) that enable the treatment frequency to be reduced to once or twice a day. In another embodiment, the insulin dosage is increased correspondingly with decreasing frequency of administration. In another embodiment, the Exenatide dosage is increased correspondingly with decreasing frequency of administration. Each type of coating, absorption enhancer, dosage form, etc, that inhibits digestion of the composition in the stomach represents a separate embodiment of the present invention.

Methods of measuring insulin levels are well known in the art. In one embodiment, levels of recombinant insulin are measuring using a human insulin radio-immunoassay (RIA) kit, e.g. the kit manufactured by Linco Research Inc, (St. Charles, Mo.). In another embodiment, levels of C peptide are measured as well, to determine the relative contributions of endogenous and exogenous insulin to observed rises in insulin levels. In another embodiment, insulin ELISA kits are used. In another embodiment, insulin levels are measured by any other method known in the art. In another embodiment, Exenatide levels are measured by a method known in the art. Each possibility represents a separate embodiment of the present invention.

In another embodiment, a multiparticulate dosage forms is used to inhibit digestion of the composition in the stomach. In another embodiment, a multiparticulate dosage forms is used to inhibit digestion of the composition in the stomach.

In another embodiment, the present invention provides a method for oral administration of a protein with an enzymatic activity to a subject, whereby a substantial fraction of the protein retains the enzymatic activity after absorption through an intestinal mucosal barrier of the subject, comprising administering orally to the subject a pharmaceutical composition comprising the protein, a protease inhibitor, and an absorption enhancer, thereby orally administering a protein with an enzymatic activity to a subject.

In another embodiment, the present invention provides a method for oral administration of a protein with an enzymatic activity to a subject, whereby a substantial fraction of the protein retains the enzymatic activity after absorption through an intestinal mucosal barrier of the subject, comprising administering orally to the subject a pharmaceutical composition comprising the protein, a protease inhibitor, and SNAC or SNAD, thereby orally administering a protein with an enzymatic activity to a subject.

In another embodiment, the present invention provides a method for oral administration of insulin to a subject, whereby a substantial fraction of insulin retains its activity after absorption through an intestinal mucosal barrier of the subject, comprising administering orally to the subject a pharmaceutical composition comprising insulin, a protease inhibitor, and SNAC or SNAD, thereby orally administering a protein with an enzymatic activity to a subject. In another embodiment, the present invention provides a method for oral administration of Exenatide to a subject, whereby a substantial fraction of Exenatide retains its activity after absorption through an intestinal mucosal barrier of the subject, comprising administering orally to the subject a pharmaceutical composition comprising Exenatide at least one protease inhibitor, and SNAC or SNAD, thereby orally administering a protein with an enzymatic activity to a subject.

In another embodiment, the present invention provides a method for oral administration of a protein with an enzymatic activity to a subject, whereby a substantial fraction of the protein retains the enzymatic activity after absorption through an intestinal mucosal barrier of the subject, comprising administering orally to the subject a pharmaceutical composition comprising the protein, at least one protease inhibitor, SNAC or SNAD, and an omega-3 fatty acid, thereby orally administering a protein with an enzymatic activity to a subject. In another embodiment, the present invention provides a method for oral administration of a protein with an enzymatic activity to a subject, whereby a substantial fraction of the protein retains the enzymatic activity after absorption through an intestinal mucosal barrier of the subject, comprising administering orally to the subject a pharmaceutical composition comprising the protein, at least one protease inhibitor, and SNAC or SNAD, EDTA (or a salt thereof), and an omega-3 fatty acid, thereby orally administering a protein with an enzymatic activity to a human subject.

In another embodiment, the present invention provides a method for oral administration of insulin to a subject, whereby a substantial fraction of insulin retains its activity after absorption through an intestinal mucosal barrier of the subject, comprising administering orally to the subject a pharmaceutical composition comprising insulin, at least one protease inhibitor, SNAC or SNAD, an omega-3 fatty acid, and Na-EDTA, thereby orally administering a protein with an enzymatic activity to a subject. In another embodiment, the present invention provides a method for oral administration of Exenatide to a subject, whereby a substantial fraction of Exenatide retains its activity after absorption through an intestinal mucosal barrier of the subject, comprising administering orally to the subject a pharmaceutical composition comprising Exenatide, at least one protease inhibitor, SNAC or SNAD, an omega-3 fatty acid, and Na-EDTA, thereby orally administering a protein with an enzymatic activity to a subject.

In another embodiment, the present invention provides a method for treating diabetes mellitus in a human subject, comprising administering orally to the subject a pharmaceutical composition comprising an insulin, at least one protease inhibitor, and SNAC or SNAD, thereby treating diabetes mellitus. In another embodiment, the present invention provides a method for treating diabetes mellitus in a human subject, comprising administering orally to the subject a pharmaceutical composition comprising an insulin and at least one protease inhibitor, and SNAC or SNAD, and omega-3 fatty acid thereby treating diabetes mellitus. In another embodiment, the present invention provides a method for treating diabetes mellitus in a human subject, comprising administering orally to the subject a pharmaceutical composition comprising an insulin and at least one protease inhibitor, and SNAC or SNAD, EDTA (or a salt thereof), and omega-3 fatty acid thereby treating diabetes mellitus.

In another embodiment, the present invention provides a method for treating diabetes mellitus in a human subject, comprising administering orally to the subject a pharmaceutical composition comprising an Exenatide, at least one protease inhibitor, and SNAC or SNAD, thereby treating diabetes mellitus. In another embodiment, the present invention provides a method for treating diabetes mellitus in a human subject, comprising administering orally to the subject a pharmaceutical composition comprising an Exenatide and at least one protease inhibitor, and SNAC or SNAD, and omega-3 fatty acid thereby treating diabetes mellitus. In another embodiment, the present invention provides a method for treating diabetes mellitus in a human subject, comprising administering orally to the subject a pharmaceutical composition comprising an Exenatide and at least one protease inhibitor, and SNAC or SNAD, EDTA (or a salt thereof), and omega-3 fatty acid thereby treating diabetes mellitus.

In one embodiment, the diabetes mellitus is Type I diabetes. In another embodiment, the diabetes mellitus is Type II diabetes. In another embodiment, the diabetes mellitus is insulin-dependent diabetes. In another embodiment, the diabetes mellitus is non-insulin-dependent diabetes. In another embodiment, the diabetes mellitus is any other type of diabetes known in the art. Each possibility represents a separate embodiment of the present invention.

In one embodiment, three treatments a day of the insulin composition are administered. In another embodiment, two treatments a day are administered. In another embodiment, four treatments a day are administered. In another embodiment, one treatment a day is administered. In another embodiment, more than four treatments a day are administered. Each possibility represents a separate embodiment of the present invention.

Any of the methods of the present invention may utilize, in various embodiments, any of the compositions of the present invention.

In another embodiment, the present invention provides a composition for oral administration of insulin, comprising an insulin protein at least one protease inhibitor, and SNAG or SNAD, whereby a substantial fraction of the insulin retains the enzymatic activity after absorption through an intestinal mucosal barrier of a human subject.

In one embodiment, the present invention provides the use of a protein, at least one protease inhibitor, and SNAC or SNAD in the manufacture of a medicament for oral administration of a protein with an enzymatic activity to a subject, whereby a substantial fraction of the protein retains the enzymatic activity after absorption through an intestinal mucosal barrier of the subject. In one embodiment, the present invention provides the use of a protein, at least one protease inhibitor, SNAC or SNAD, and an omega-3 fatty acid in the manufacture of a medicament for oral administration of a protein with an enzymatic activity to a subject, whereby a substantial fraction of the protein retains the enzymatic activity after absorption through an intestinal mucosal barrier of the subject. In one embodiment, the present invention provides the use of a protein, at least one protease inhibitor, SNAC or SNAD, Na-EDTA, and an omega-3 fatty acid in the manufacture of a medicament for oral administration of a protein with an enzymatic activity to a subject, whereby a substantial fraction of the protein retains the enzymatic activity after absorption through an intestinal mucosal barrier of the subject.

In one embodiment, the present invention provides the use of an insulin protein, at least one protease inhibitor, and SNAC or SNAD in the manufacture of a medicament for treating diabetes mellitus in a subject. In one embodiment, the present invention provides the use of an insulin protein, at least one protease inhibitor, SNAC or SNAD, and an omega-3 fatty acid in the manufacture of a medicament for treating diabetes mellitus in a subject. In one embodiment, the present invention provides the use of an insulin protein, at least one protease inhibitor, SNAC or SNAD, Na-EDTA, and an omega-3 fatty acid in the manufacture of a medicament for treating diabetes mellitus in a subject.

In one embodiment, the present invention provides the use of an Exenatide protein, at least one protease inhibitor, and SNAC or SNAD in the manufacture of a medicament for treating diabetes mellitus in a subject. In one embodiment, the present invention provides the use of an Exenatide protein, at least one protease inhibitor, SNAC or SNAD, and an omega-3 fatty acid in the manufacture of a medicament for treating diabetes mellitus in a subject. In one embodiment, the present invention provides the use of an Exenatide protein, at least one protease inhibitor, SNAC or SNAD, Na-EDTA, and an omega-3 fatty acid in the manufacture of a medicament for treating diabetes mellitus in a subject.

In one embodiment, methods and compositions of the present invention have the advantage of more closely mimicking physiological insulin secretion by the pancreas. When insulin is secreted into the portal vein, the liver is exposed to a greater insulin concentration than peripheral tissues. Similarly, insulin administered according to the present invention reaches the intestine and is absorbed in the body through the intestine and through the portal system to the liver. This absorption route thus resembles the physiological secretion of insulin by the pancreas, enabling, in this embodiment, delicate control of the blood glucose level and the metabolic activities of the liver and the peripheral organs controlled by insulin. By contrast, when insulin is administered to insulin-deficient diabetic patients via the peripheral venous system, the concentration of insulin in the portal vein is similar to that in the peripheral circulation, resulting in hypoinsulinemia in the portal vein and the liver and hyperinsulinemia in the peripheral venous system. This leads, in one embodiment, to an abnormal pattern of glucose disposal.

In another embodiment, different constituents of compositions of the present composition are absorbed at different rates from the intestinal lumen into the blood stream. The absorption of the bile acid, in one embodiment, is significantly faster than the absorption of insulin.

For this reason, in another embodiment, a drug regimen involving ingestion of a pair of pills at spaced intervals, e.g., a second pill containing a higher concentration of enhancer is taken at a defined interval (e.g. 30 minutes) after the first pill. In another embodiment, certain of the constituents are microencapsulated to enhance the absorption of the insulin into the system. In another embodiment, certain of the constituents are microencapsulated to enhance the absorption of the Exenatide into the system.

In one embodiment, a treatment protocol of the present invention is therapeutic. In another embodiment, the protocol is prophylactic. Each possibility represents a separate embodiment of the present invention.

In another embodiment, solid carriers/diluents for use in methods and compositions of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In another embodiment, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), surfactants (e.g. sodium lauryl sulfate), permeation enhancers, solubilizing agents (e.g., glycerol, polyethylene glycerol), antioxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In some embodiments, the dosage forms of the present invention are formulated to achieve an immediate release profile, an extended release profile, or a delayed release profile. In some embodiments, the release profile of the composition is determined by using specific excipients that serve for example as binders, disintegrants, fillers, or coating materials. In one embodiment, the composition will be formulated to achieve a particular release profile as known to one skilled in the art.

In one embodiment, the composition is formulated as an oral dosage form. In one embodiment, the composition is a solid oral dosage form comprising tablets, chewable tablets, or capsules. In one embodiment the capsules are soft gelatin capsules. In another embodiment, capsules as described herein are hard-shelled capsules. In another embodiment, capsules as described herein are soft-shelled capsules. In another embodiment, capsules as described herein are made from gelatine. In another embodiment, capsules as described herein are made from plant-based gelling substances like carrageenans and modified forms of starch and cellulose.

In other embodiments, controlled- or sustained-release coatings utilized in methods and compositions of the present invention include formulation in lipophilic depots (e.g. fatty acids, waxes, oils).

The compositions also include, in another embodiment, incorporation of the active material into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance. In another embodiment, particulate compositions of the active ingredients are coated with polymers (e.g. poloxamers or poloxamines)

In another embodiment, the compositions containing the insulin and omega-3 fatty acid are delivered in a vesicle, e.g. a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid). In another embodiment, the compositions containing the Exenatide and omega-3 fatty acid are delivered in a vesicle, e.g. a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the active ingredients of compositions of the present invention are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions.

Each of the above additives, excipients, formulations and methods of administration represents a separate embodiment of the present invention.

In one embodiment, the term "treating" refers to curing a disease. In another embodiment, "treating" refers to preventing a disease. In another embodiment, "treating" refers to reducing the incidence of a disease. In another embodiment, "treating" refers to ameliorating symptoms of a disease. In another embodiment, "treating" refers to inducing remission. In another embodiment, "treating" refers to slowing the progression of a disease.

EXPERIMENTAL DETAILS SECTION

Example 1

Insulin, SNAC, and Protease Inhibitors Oral Formulations

Materials and Experimental Methods

Formulation

Formulations were prepared containing: (1) 6 mg insulin, 250 mg SNAC, 125 mg SBTI, (2) 6 mg insulin, 2.5 mg Aprotinin, 125 mg SBTI, (3) 6 mg insulin, 250 mg SNAC, 2.5 mg Aprotinin, 125 mg SBTI, (4) 6 mg insulin, 250 mg SNAC. The formulations were stored in the refrigerator (4° C.) until dosing.

Results

Figure 2:
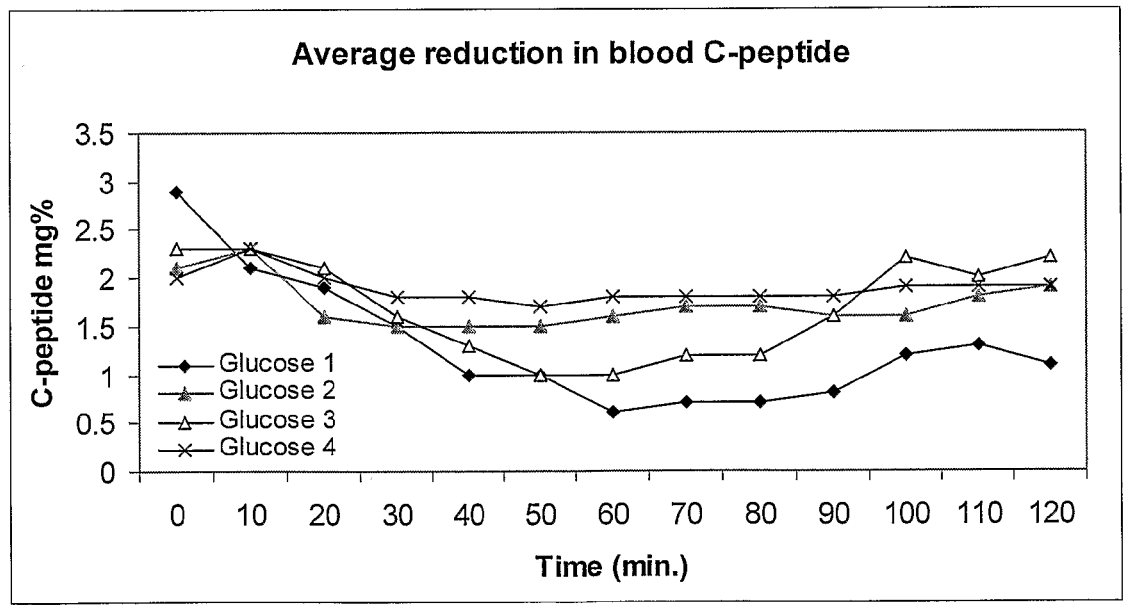
FIG. 2 is a graph showing the changes in blood C-peptide levels after treatment with the formulations of the invention.

In the next experiment, the formulations as describes in the "Formulation" section were orally consumed by 3 healthy human subjects. As shown in FIG. 1, blood glucose levels were significantly reduced and more stable in human subjects treated with formulations (1) and (3). These results suggest that formulations comprising a combination of a protease inhibitor and SNAC are superior to formulations comprising only SNAC. Specifically, the combination of SNAC and SBTI is superior to any other formulation used. It is important to notice that the effect of SNAG and a protease inhibitor is synergistic because formulations consisting insulin and a single protease inhibitor do not have a blood glucose lowering effect- no differences in the reduction of blood glucose levels were observed in previous experiment with the same formulations comprising a single protease inhibitor (SBTI or Aprotinin). Thus, the results regarding the reduction in blood glucose levels with insulin and a combination of SNAC and at least one protease inhibitor was unexpected. The formulation comprising SNAC and SBTI had a synergistic, utmost effect in lowering blood glucose levels As shown in FIG. 2, blood C-peptide levels were significantly reduced in human subjects treated with formulation (1) and (3). These results also suggest that the combination of SNAC and a protease inhibitor such as SBTI had a synergistic effect in lowering blood C-peptide levels.

It should be emphasized that no reduction of C-peptide levels were observed in a previous experiment wherein formulations comprising a single protease inhibitor (SBTI or Aprotinin) were used. Thus, the results regarding the reduction in blood C-peptide levels with insulin and a combination of a protease inhibitor such as SBTI and SNAG was unexpected.

Example 2

Optimization of Source of Omega-3 Fatty Acids

Various omega-3 fatty acids or sources of omega-3 fatty acids (e.g. those listed above in the specification) are compared for their ability to preserve insulin following oral administration in methods and compositions of the present invention. Insulin tablets or capsules are formulated as described in the above Examples, except that the insulin is dissolved in the alternate source instead of in fish oil. The most effective source of omega-3 fatty acids is used in subsequent Examples.

Example 3

Optimization of a Protease Inhibitor

Various protease inhibitors (either non-toxic or having an acceptable toxicity profile; e.g. those listed above in the specification) are compared for their ability to preserve insulin following oral administration in methods and compositions of the present invention. Insulin and/or Exenatide tablets or capsules are formulated as described in the above Examples, except that the alternate protease inhibitors are substituted for SBTI and/or Aprotinin. Amounts of the protease inhibitors are also varied, to determine the optimal amounts. The most effective protease inhibitor/amount is used in subsequent Examples.

Example 4

Optimization of an Enhancer

Various enhancers (e.g. those listed above in the specification) are compared for their ability to facilitate absorption of insulin following oral administration in methods and compositions of the present invention. Insulin tablets or capsules are formulated as described in the above Examples, except that the alternate enhancers are substituted for EDTA. Amounts of the enhancers are also varied, to determine the optimal amounts. The most effective enhancer/amount is used in subsequent experiments.

Example 5

Optimization of Type and Amount of Insulin

Various types and amounts of insulin e.g. those listed above in the specification) are compared for their ability to regulate blood sugar in methods and compositions of the present invention. Insulin tablets or capsules are formulated as described in the above Examples, except that the type and amount of insulin is varied. The most effective type/amount of insulin is used in clinical trials.

What is claimed is:

1. A single, solid oral pharmaceutical composition comprising an insulin; a protease inhibitor; and a compound in an effective amount to synergistically increase the bioavailability of said insulin, wherein said protease inhibitor is selected from aprotonin and soy bean trypsin inhibitor (SBTI), and wherein said compound is selected from the group consisting of N-(8-[2-hydroxybenzoyl]amino)caprylate (SNAC), N-(10-[2-hydroxybenzoyl]amino)decanoate (SNAD), a salt of said SNAC or said SNAD, and a combination thereof.

2. The composition of claim 1, wherein said insulin is a recombinant insulin.

3. The composition of claim 1, wherein said compound is a salt of said SNAC or said SNAD, and said salt is selected from the group consisting of a monosodium salt, a disodium salt, and a combination thereof.

4. The composition of claim 1, further comprising an omega-3 fatty acid.

5. The composition of claim 1, further comprising EDTA or a salt thereof.

6. The composition of claim 1, further comprising a coating that inhibits digestion of said composition in a stomach of a subject; an enteric coating; or a gelatin coating.

7. A method of treating diabetes mellitus in a subject in need thereof, the method comprising administering orally to said subject the single, solid oral composition of claim 1.

8. The method of claim 7, wherein said pharmaceutical composition further comprises an omega-3 fatty acid.

9. The method of claim 7, wherein said pharmaceutical composition further comprises EDTA or a salt thereof.

10. The method of claim 7, wherein said pharmaceutical composition further comprises a coating that inhibits digestion of said pharmaceutical composition in a stomach of a subject; an enteric coating; or a gelatin coating.

11. The composition of claim 1, wherein said protease inhibitor and said compound increase the bioavailability of said insulin by 10-100%.

12. A method for treating diabetes mellitus in a subject in need thereof, the method comprising administrating orally to said subject the single, solid oral pharmaceutical composition of claim 1.

13. The method of claim 12, wherein said insulin is recombinant insulin.

14. The method of claim 12, wherein said pharmaceutical composition further comprises an omega-3 fatty acid.

15. The method of claim 12, wherein said pharmaceutical composition further comprises EDTA or a salt thereof.

16. The method of claim 12, wherein said pharmaceutical composition further comprises a coating the inhibits digestion of said pharmaceutical composition in a stomach of a subject; an enteric coating; or a gelatin coating.

17. A single oral pharmaceutical composition consisting of insulin; a protease inhibitor; a compound in an effective amount to synergistically increase the bioavailability of said insulin; an agent selected from the group consisting of an omega-3 fatty acid, EDTA or a salt thereof and a combination thereof; and optionally a coating that inhibits digestion of said pharmaceutical composition in a stomach of a subject, wherein said protease inhibitor is selected from aprotonin and soy bean trypsin inhibitor (SBTI) and wherein said compound is selected from the group consisting of N-(8-[2-hydroxybenzoyl] amino)caprylate (SNAC), N-(10-[2-hydroxybenzoyl]amino)decanoate (SNAD), a salt of said SNAC or said SNAD, and a combination thereof.

18. The composition of claim 17, wherein said insulin is a recombinant insulin.

19. A method for oral administration of a recombinant insulin to a subject in need thereof, the method comprising administering orally to said subject the single, solid oral pharmaceutical composition of claim 17.

20. A method for treating diabetes mellitus in a subject in need thereof, the method comprising administering orally to said subject the single, solid oral pharmaceutical composition of claim 17.

21. The composition of claim 17, wherein said protease inhibitor and said compound increase the bioavailability of said insulin by 10-100%.

* * * * *